April 4, 1961 M. E. HENRICKE Plant Pat. 2,041
HYDRANGEA MACROPHYLLA PLANT
Filed Jan. 18, 1960
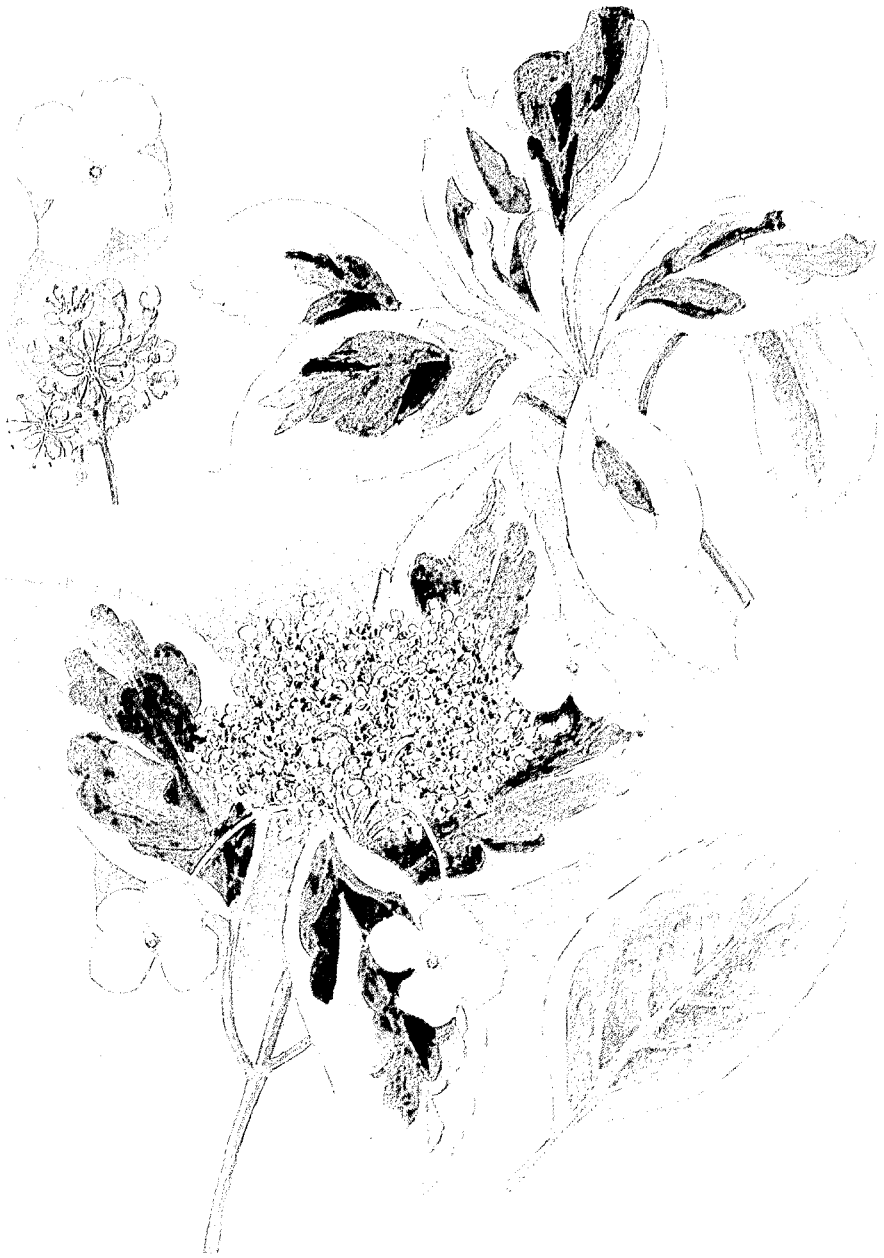
INVENTOR
Mary Estelle Henricke,
by:- John H Kinnard,
her ATTY.

United States Patent Office

Plant Pat. 2,041
Patented Apr. 4, 1961

2,041

HYDRANGEA MACROPHYLLA PLANT

Mary Estelle Henricke, Portland, Oreg., assignor to The Wayside Gardens Company, Mentor, Ohio Filed Jan. 18, 1960, Ser. No. 3,217

1 Claim. (Cl. 47—60)

This invention relates to a new variety of hydrangea plant which is a *Hydrangea macrophylla* variegated.

The new variety of hydrangea plant was produced by selecting one branch, a sport showing variegations, of a *Hydrangea macrophylla* plant and producing cuttings therefrom over a period of years, and selecting from the cuttings the more variegated specimens and reproducing them, in turn, by cuttings, until the present variety was obtained.

The parentage is unknown.

The plant was first asexually reproduced in Portland, Oregon, by soft wood cuttings.

The color drawing shows at the lower left a typical terminal of a stalk with leaves, buds, and blooms thereon, at the upper left an enlarged picture of some of the florets and buds, at the upper right a typical leaf arrangement, and at the lower right the underside of a typical leaf.

In designating colors herein, the British Color Council Horticulture Color Chart and the Maerz and Paul Dictionary of Color are used. References to the former are designated "Chart," followed by sheet and number. References to the latter are designated "Plate," followed by letter and number.

*Root structure*

The root structure is the usual fibrous mass for hydrangea plants, being average in size and shallow to medium in depth. The root has good weather resistance when protected, but the exposed plant tends to die back to the ground if unprotected at temperatures below zero. The roots have a wide tolerance for soils, but soil conditions affect the color of the blooms, a soil with an acid reaction tending to produce blue blooms and soil with an alkaline reaction tending to produce pink blooms.

*Exposed plant structure*

The exposed plant is in the form of a hardy shrub of generally upright bushy growth, rounded at the top, having a height and spread each of about four to five feet, and generally symmetrical in contour. It has medium to vigorous growth, and good resistance to low temperatures when protected, but poor when unprotected, dying back to the ground at temperatures below zero. Its drought resistance is about usual for hydrangea plants, but it has good tolerance of wet seasons. It prefers moderate sunshine to almost total shade. It grows well in any exposure suitable for other hydrangea plants. It prefers normal drainage and grows satisfactorily in any good type of garden soil.

*Individual parts of the exposed plant*

The main stalks grow generally upright. They are relatively stiff and adequate to support well the foliage, bloom, and fruit. The new growth is highly variegated in color with a yellow cast. The main stalks range in length from three feet to five or six feet on the average, and grow divergently from the base. They are generally smooth in texture.

The plant is not heavily branched. The branches generally are arranged oppositely and are light green in color with a smooth texture. They are medium straight, stiff, but somewhat flexible and adequate to support the bloom and foliage.

The foliage is dense and abundant with the leaves oppositely arranged.

As illustrated by the leaf next to the top in the upper right hand view, the bodies of the new leaves are, on the upper side, a mimosa yellow, Chart Sheet 143, Number 602/2. The bodies of the mature leaves are white, Plate 9–A–1 to 9–B–1, with a green marking, Plate No. 21–L–9. This is mottled with about three shades of green ranging from a gray green which is the lightest color to a gray olive green and then to a dark green, these three colors being comparable to Chart Sheet 197, Number 000858/2, leek green; Sheet 198, Number 000861, sage green; and Sheet 197, Number 000858, leek green.

The markings on the underside of the leaf are quite uniform with no clear cut divisions. They are mostly paler than the upper side, ranging from the above leek green Number 000858/2 to the sage green Number 000861. The underside of the main rib is a green, Plate 18–B–6.

The margins of the leaves are serrated beginning about one and one-half inches from the tip. The leaves are variegated in color and of medium size and thickness, having the usual length, width, shape, margin, base, and apex arrangement as other hydrangea plants. They are smooth and glossy on both the upper and lower faces.

Their persistency on the plant is usual. They have an unusual characteristic in that their color is variegated.

The petioles or leaf stems are a light green, Chart Sheet 197, Number 000858/2. They are of the usual length, surface texture, and strength. There are no stipules.

*Blooms*

The plant blooms well in zone 3 south which it prefers, but it does well also, with heavy winter protection, farther north. It blooms most effectively in moderate sun to shade, but otherwise is relatively indifferent as to exposure. The best quality of blooms is obtained in a wet, cool season in moist, slight alkaline to slightly acid, rich loam. The quality of the blooms decreases in dry hot seasons and in poor well drained soils.

The variegation of the blooms develops best in partial shade, but the color is affected by the soil condition, acid reaction tending to produce blue and alkaline tending to produce pink.

The blooming period is the usual one from midsummer through late summer into early fall, during which period the plant blooms continuously.

Cutting the blooms has the same effect as in the case of other hydrangea plants.

The buds are of the usual size, form, and aspect and are supported in the usual upright position. Their color prior to blooming and during blooming does not appear to be unusual. They do not have any unusual characteristics.

The peduncles average from one inch to two inches in length and have the usual surface texture and color.

Each plant bears the usual number of blooms. The blooms average, in diameter, about three to six inches, and are borne in heads. They have no unusual qualities or characteristics.

The main large floret, together with its stem, as illustrated in the upper left hand view, is white. The small florets are reddish purple, Plate No. 43–F–7. The underside of the petals is a slightly lighter purple, Plate No. 42–B–4. The pistils and stamens are a deep brownish purple, Plate No. 55–L–6. The color of the calyx is generally chalcedony yellow, Plate 18–J–1. The buds are generally a pale green, Plate 18–I–2, varying at the underside of the florets to purplish, comparable to Chart 42–B–4.

The unusual feature of the plant resides in the foliage and the variegation in the leaf coloring which make it a colorful garden subject which can be used advantageously in producing overall color effects, particularly during mid and late summer, in plantings of shrubs and perennials.

Having shown and described my new variety of variegated *Hydrangea macrophylla* plant, I claim:

The new and distinct variety of *Hydrangea macrophylla* plant herein shown and described.

No references cited.